United States Patent
Spallek et al.

[11] Patent Number: 5,897,532
[45] Date of Patent: Apr. 27, 1999

[54] GRIPPING STRIP FOR PREFILLED DISPOSABLE SYRINGES

[75] Inventors: Michael Spallek, Ingelheim; Andreas Geiger, Woerrstadt, both of Germany; John W. Pellow, Lebanon, Pa.

[73] Assignee: Schott Glas, Mainz, Germany

[21] Appl. No.: 09/092,287

[22] Filed: Jun. 5, 1998

[30] Foreign Application Priority Data

Jun. 6, 1997 [DE] Germany .............................. 197 23 851

[51] Int. Cl.$^6$ ............................................... A61M 5/00
[52] U.S. Cl. ............................................ 604/187; 604/227
[58] Field of Search ................................. 604/187, 218, 604/220, 221, 227, 232, 235; 128/DIG. 6, 919; 403/83, 88, 92, 93, 97, 98, 102

[56] References Cited

U.S. PATENT DOCUMENTS

| | | | |
|---|---|---|---|
| 3,921,633 | 11/1975 | Tischlinger | 604/227 |
| 3,978,858 | 9/1976 | Tischlinger | 604/187 |
| 4,704,105 | 11/1987 | Adorjan et al. | |
| 5,338,309 | 8/1994 | Imbert | 604/187 |
| 5,364,369 | 11/1994 | Reynolds | |
| 5,554,133 | 9/1996 | Haffner et al. | 604/227 |

FOREIGN PATENT DOCUMENTS

| | | | |
|---|---|---|---|
| 39 24 830 A1 | 2/1991 | Germany | |
| 44 34 644 A1 | 4/1996 | Germany | |
| 0020266 | 12/1929 | Netherlands | 604/227 |
| WO 91/01152 | 2/1991 | WIPO | |
| WO 92/08507 | 5/1992 | WIPO | |

*Primary Examiner*—Corrine M. McDermott
*Assistant Examiner*—Sharon Finkel
*Attorney, Agent, or Firm*—Michael J. Striker

[57] ABSTRACT

A gripping strip for prefilled disposable syringes having a syringe cylinder. The gripping strip has a gripping strip element formed as a separate synthetic plastic part fixedly mountable on the syringe cylinder, a plate-shaped abutment provided on the gripping strip element and having a hollow cylindrical receptacle with an outer diameter which is adapted to be smaller than an inner diameter of the syringe cylinder, arresting elements provided in a region of an outer surface of the gripping strip element for mounting with the syringe cylinder in a complimentary inner undercut of the syringe cylinder, a safety ring insertable in an interior of the receptacle for maintaining a working connection, the safety ring being connected with the interior of the receptacle of one piece through locations of desired breakage in an unsecured position, so that during placing the syringe cylinder over the receptacle it is displaceable into a securing position. The receptacle has an outer surface which is formed of peripheral portions with gaps therebetween, the arresting elements being arranged in the gaps for a form-locking operative connection with the inner undercut of the syringe cylinder.

8 Claims, 2 Drawing Sheets

GRIPPING STRIP FOR PREFILLED DISPOSABLE SYRINGES

BACKGROUND OF THE INVENTION

The present invention relates to a gripping strip for disposable syringes having a syringe cylinder with an end on which the gripping strip is fixedly mounted as a separate synthetic plastic part.

In this construction the gripping strip has a plate-shaped abutment with a hollow cylindrical receptacle whose outer diameter is smaller than the inner diameter of the syringe cylinder, and in the region of the outer surface arresting elements are formed for a form-locking operative connection for mounting on the syringe cylinder. The syringe cylinder has an inner undercut which is complementary to the arresting elements. In the interior of the receptacle, a safety ring is inserted for maintaining the operative connection. Syringes for medical and diagnostic purposes have a gripping strip on the syringe cylinder which is formed as a counter support during pressing of the piston into the syringe cylinder for application process, whether its manual or by means of a injection pump.

This gripping strip is also identified as a finger support and a cylinder gripping plate. The connection of the gripping strip with the syringe cylinder must withstand pulling out forces, up to 100 N.

There are two basic concepts for arranging the gripping strip of the syringe cylinder. In accordance with the first concept, the gripping strip is formed of one piece with the syringe cylinder during its manufacture. Because of the geometry of the plate shaped abutment which deviates from the circular form, the gripping strip during filling interferes with the syringe, and it must have a relatively great distance between the magazine syringe bodies projecting during filling. In the case of glass syringes, a certain breakage damage and the danger of sliding of the finger during the application process exists, which was found by patients to be very unpleasant.

In accordance with a second concept from the which the present invention is derived, the gripping strip is formed as a separate synthetic plastic part and subsequently, or in other words after the filling process, is mounted on the syringe cylinder which can be composed of glass or synthetic plastic. With this concept the disadvantages of the first concept with the one-piece formed gripping strip can be eliminated.

Since the gripping strip must withstand high pulling out forces, the strength or stability of the connection of the synthetic plastic gripping strip with the syringe cylinder is especially important.

It is known to mount the syringe cylinder in the interior of the hollow cylindrical receptacle of the gripping strip. This type of mounting has a substantial disadvantage that the wall of the hollow cylindrical receptacle projects opposite to the diameter of the syringe cylinder with a sharp edge transition to the syringe cylinder. The required axial expansion of the receptacle takes over the outer surface of the syringe cylinder which is required for example, for the label. This axial extension interferes during the reception of the syringe in the injection pump, and with certain pump types prevents such a reception. On the other hand, in the known gripping strips, a relatively great synthetic plastic mass is needed for manufacture. This is on the one hand unfavorable for the disposal and on the other hand increases manufacturing costs, the features which are extremely important for disposable articles. In addition, the arrangement of the mounting of the gripping strip is relatively expensive.

In the above mentioned patent document DE 39 24 830 A1, the finger application on the syringe cylinder must be relatively simply arrestable with the use of a louver baffle cap, but such a connection withstands only low pulling out forces. As a rule, the synthetic plastic griping strip shrinks under the action of preliminary heating. This step requires substantial expenses during the manufacture, or in other words, an expensive mounting, to provide a very accurate temperature control. In addition, when the gripping strip is too cold, it can not be mounted, but when the temperature is too high, it can melt. The heating negatively influences the filling agent and also interferes with the filing in the cleaning chamber in which it is desired to obtain a flow from above downwardly, which is disturbed by the upwardly oriented heat flow.

The patent document WO 92 08507, FIG. 1 (equivalent to U.S. Pat. No. 5,364,369, FIG. 17) discloses a gripping strip for prefilled disposable syringes with the syringe cylinder, having an end with a gripping strip fixedly mounted on it as a separate synthetic plastic part. It has a plate-shaped abutment with a hollow cylindrical receptacle having an outer diameter which is smaller than the inner diameter of the syringe cylinder. An arresting element formed as a ring groove is provided in a socket-like manner on the outer surface of the hollow cylindrical receptacle, or a form-locking operative connection with the syringe cylinder which has a complementary inner edge bead.

In this known gripping strip, the receptacle is mounted in the interior of the syringe cylinder. Thereby the gripping strip does not occupy any surface of the outer casing of the syringe cylinder, there is no sharp edge transition between the gripping strip and the casing of the syringe cylinder which can cause an injury danger, and due to the geometry the syringe is insertable in injection pumps in a simple manner without any problems.

The principal disadvantage of this construction is however that the gripping strip can not withstand any high pulling out forces, since the form-locking arresting connection can be readily releasably released. The above mentioned WO 92 08507 document in FIG. 5 shows an alternative embodiment with an inner undercut on the syringe cylinder and a complimentary edge bead on the hollow cylindrical receptacle, with an additional outer arresting connection composed of a edge bead on the syringe cylinder and a claw-shaped formation on the plate-shaped abutment of the gripping strip. The pulling forces which it withstands in this embodiment are also low, since the form-locking connection can be easily broken. In addition, due to the deviation from the cylindrical shape on the base of the syringe cylinder, the insertion into the injection pumps causes certain problems.

The same is true for the above mentioned U.S. Pat. No. 5,364,369 which in FIG. 13 shows the gripping strip with the hollow cylindrical receptacle of separate peripheral portions and formed projections for an outer form-locking connection with an outer border edge formed on the edge of the syringe cylinder.

The German document DE 44 34 614 A1 discloses in FIG. 1C the above identified gripping strip which can withstand high pulling out forces. The reason is that the form-lock of the operative connection is maintained by the safety ring and is insertable in the injection pump without any problems, since a small cylinder surface is available up to the abutment of the gripping grip.

The known gripping strip requires relatively high manufacturing and mounting expenses. It must be produced with two separate parts, namely the plate-shaped abutment with the receptacle and the safety ring, and must have these parts on the device to be supplied to the manufacturing process. In addition, the material consumption is very high due to the massive design of the gripping strip part, that has the above mentioned negative consequences with respect to the disposability and manufacturing cost, which is exceptionally important in the manufacture of mass articles.

SUMMARY OF THE INVENTION

Accordingly, it is an object of the present invention to provide a gripping strip of the above mentioned general type, which avoids the disadvantages of the prior art.

More particularly, it is an object of present invention to provide a gripping strip which has lower manufacturing and mounting expenses as well as material consumption.

In keeping with these objects and with others which will become apparent hereinafter, one feature of present invention resides, briefly stated, in a gripping strip in which the safety ring is connected of one piece with the receptacle through points of desired breakage in an unsecured position, and during placing of the ejection cylinder over the receptacle is displaced to the secured position, and the outer surface of the receptacle is formed only in peripheral portions so that in the gaps therebetween, the arresting elements for the form-locking operative connection with the inner undercut of the ejection cylinder are formed.

When the gripping strip is designed in accordance with the present invention, it is formed as a one-piece part which is produced in a single process. The gripping part is very simply mountable by manual placing of the syringe cylinder onto the whole cylindrical receptacle and insertion of the safety ring. The gripping strip requires relatively little synthetic plastic material, which is very favorable for its disposal and the manufacturing costs.

In accordance with a further feature of the present invention, the arresting elements are formed by hook-shaped arresting tongues which allow a simple and thereby reliable connection.

An especially durable seat of the safety ring in accordance with the present invention is possible when connecting elements are formed on the receptacle and on the safety ring for a snap connection so that the safety ring is movable from the secure position only in a breaking manner.

Preferably, the gripping part is formed as an injection molded part and composed of a thermoplastic material, for example polyolefin (polypropylene, polyethylene), but preferably of polycarbonate (PC) or polyoxymethylene (POM).

Preferably, in the gaps between the peripheral portions from the outer surface of the receptacle, the connecting elements are formed for the snap connection with the safety ring. This embodiment is also material-saving and provides a fixed connection of the safety ring.

An especially favorable handling of the syringe, in which no slippage of the finger occurs on the gripping strip during application as well as a further material saving is possible, is achieved when in accordance with a second embodiment of the invention, a grate structure is formed in the flange-like abutment and is open at the side facing the syringe cylinder.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

The drawings show a gripping strip for prefilled disposable syringes, which is fixedly mounted on a syringe cylinder (not shown) and in particular on its one end as a separate synthetic plastic part. The gripping strip has a plate-shape abutment I with a hollow cylindrical receptacle 2 for mounting with the syringe cylinder. The outer diameter of the receptacle 2 is smaller than the inner diameter of the syringe cylinder, so that the gripping strip is mountable in the interior of the syringe cylinder and thereby does not form an outwardly projecting edge.

Figure 1:
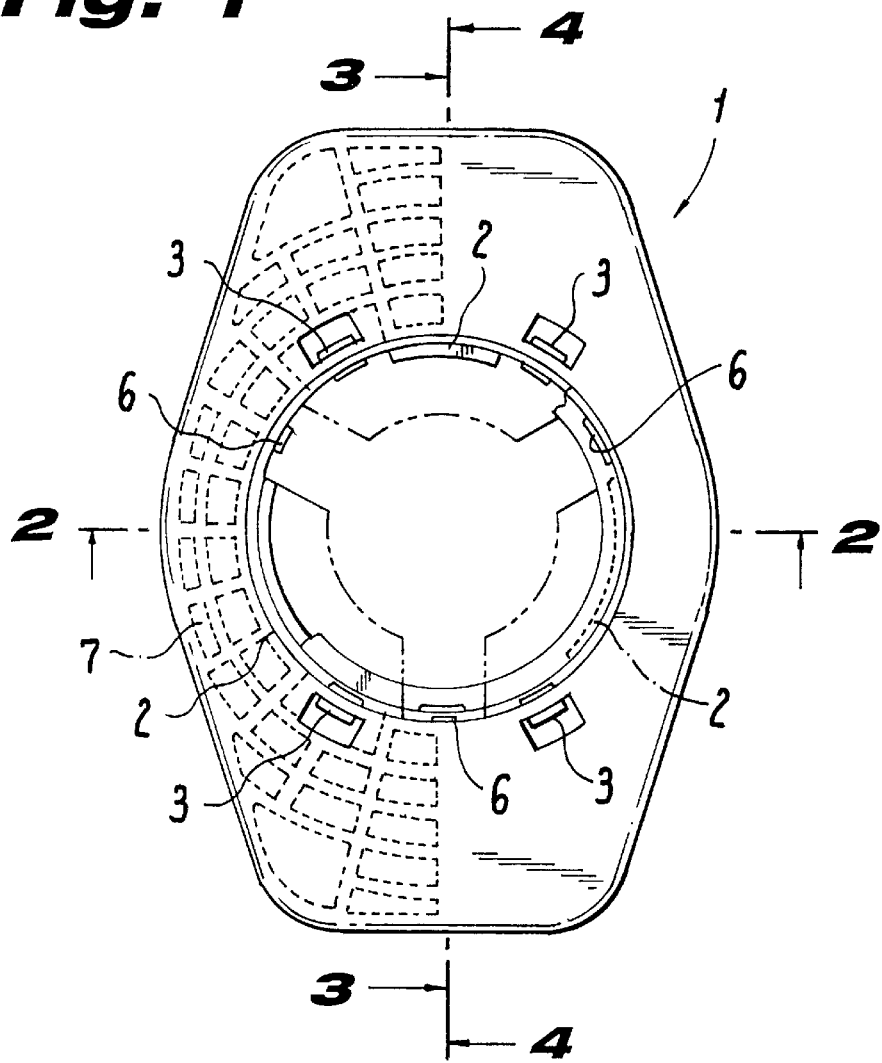
FIG. 1 is a plan view of a gripping strip for a prefilled disposable syringe in accordance with the present invention.

As can be seen from FIG. 1, in the shown embodiment of the disposable syringe, the outer surface of the receptacle 2 is not a continuous surface, but instead is formed substantially in three peripheral portions. They are identified with reference numerals 2. Peripheral arresting elements 3 are formed in the gaps between the peripheral portions. In the shown embodiments, there are four arresting elements for a form-locking operative connection with an edge-side inner ring collar (undercut) of the syringe cylinder. The arresting elements simultaneously perform a guiding function for the syringe cylinder in the gaps of the peripheral portions 2 of the outer surface of the receptacle. The arresting elements 3 in the shown embodiment are formed as, hook-shaped arresting tongues. They allow an especially simple clamping of the syringe cylinder and operate so that the gripping strip can withstand high pulling forces.

Figure 2:
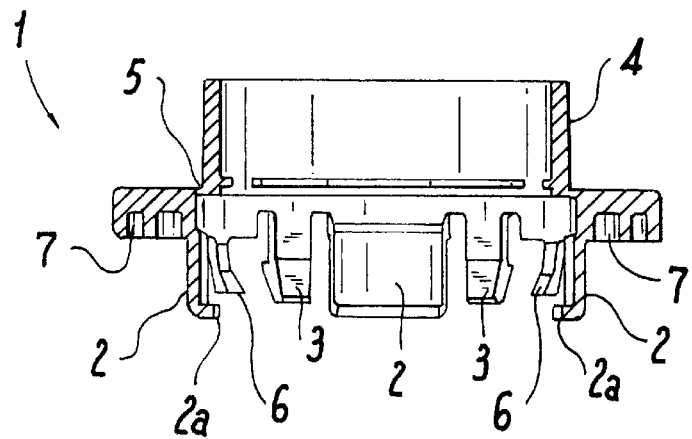
FIG. 2 is a view showing the section of the inventive disposable syringe taking along the line A—A in FIG. 1.
Figure 3:
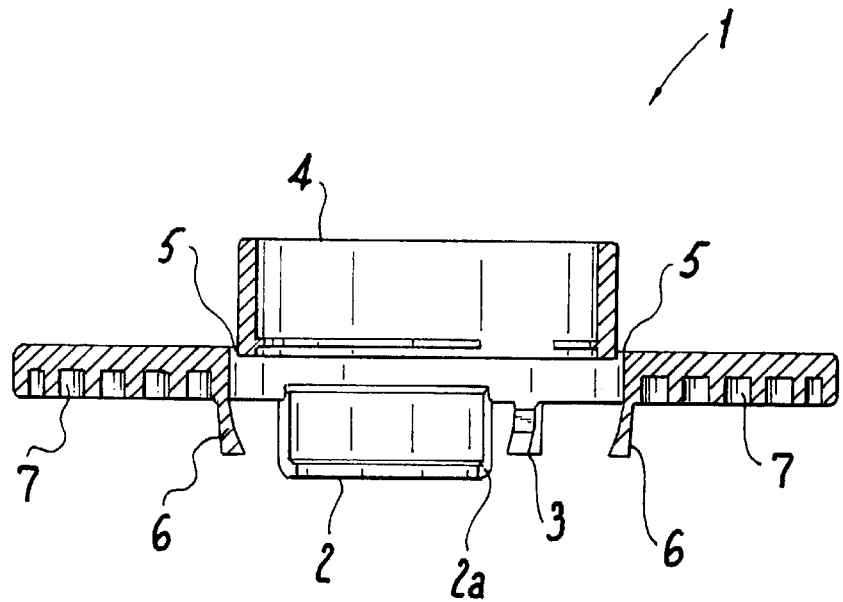
FIG. 3 is a view showing a section of the inventive disposable syringe taken along the line B—B in FIG. 1.
Figure 4:
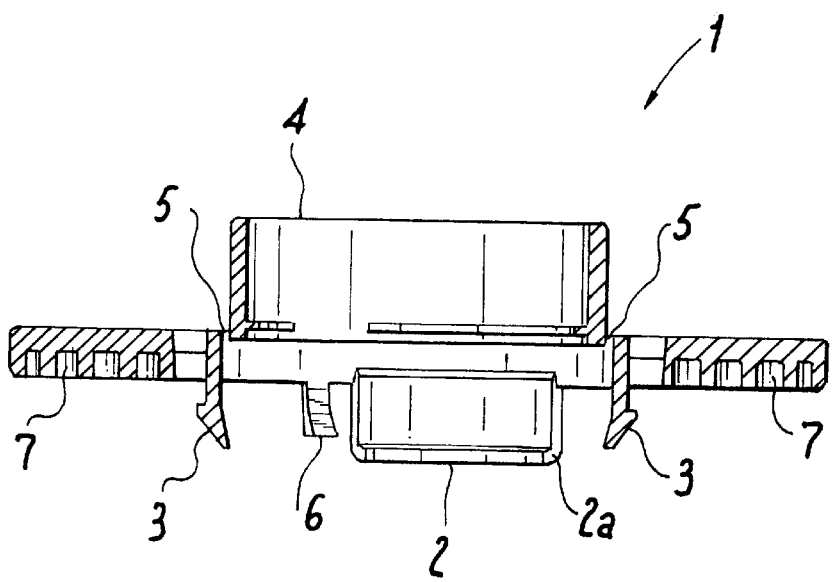
FIG. 4 is a view showing a section of the inventive disposable syringe taken along the line C—C in FIG. 1.

The gripping strip in accordance with FIG. 1 further has a safety ring 4. The safety ring is mountable in the interior of the receptacle 2 for maintaining the operative connection between the peripheral arresting elements 3 and the edge-side inner collar of the syringe cylinder. This safety ring, as in particular can be seen from FIG. 2, is connected of one piece with the interior of the receptacle 2 through points of desired breakage 5 in a unsecured position of FIG. 2. During the placing of the syringe cylinder over the receptacle 2, the points of desired breakage 5 break through and the safety ring is displaced into the secure position into the interior of the receptacle, and in particular to the abutment 2a on three receiving portions 2. For blocking the safety ring in this securing position, three connecting elements shaped as arresting tongues 3 are formed for a snap connection with a corresponding counter piece on the safety ring 4. Therefore, the safety ring is movable from the securing position only when it is destroyed. The snap connecting elements 6, similarly to the arresting tongues 3, are formed in the gaps between the peripheral portions of the outer surface of the receptacle.

In accordance with the shown embodiment of the inventive gripping strip, the plate-shaped abutment 1 is formed for example with a grate structure 7. The grate structure is open at the side which faces the syringe cylinder, or in other words at the side on which the finger abuts. Thereby the finger of the operator during application obtains a particularly gripping and thereby a reliable abutment against the gripping strip and can not slide from the plate-shaped abutment.

It will be understood that each of the elements described above, or two or more together, may also find a useful application in other types of constructions differing from the types described above.

While the invention has been illustrated and described as embodied in gripping strip for prefilled disposable syringes, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A gripping strip for prefilled disposable syringes having a syringe cylinder, the gripping strip comprising a gripping strip element formed as a separate synthetic plastic part fixedly mountable on the syringe cylinder; a plate-shaped abutment provided on said gripping strip element and having a hollow cylindrical receptacle with an outer diameter which is adapted to be smaller than an inner diameter of the syringe cylinder; arresting elements provided in a region of an outer surface of said gripping strip element for mounting with the syringe cylinder in a complimentary inner undercut of the syringe cylinder; a safety ring insertable in an interior of said receptacle for maintaining a working connection, the safety ring being connected with the interior of said receptacle of one piece through points of desired breakage in a not securing position, so that during placing of the syringe cylinder over said receptacle it is displaceable into a securing position, said receptacle having an outer surface which is formed of peripheral portions with gaps therebetween, said arresting elements being arranged in said gaps for a form-locking operative connection with the inner undercut of the syringe cylinder.

2. A gripping strip as defined in claim 1, wherein said arresting elements are formed as hook shaped arresting tongues.

3. A gripping strip as defined in claim 1, further comprising connecting elements provided on said receptacle and on said safety ring for a snap connection so that said safety ring is movable from said securing position only in a destructing manner.

4. A gripping strip as defined in claim 1, further comprising connecting elements provided in said gaps between said peripheral portions of said outer surface of said receptacle for a snap connection with said safety ring.

5. A gripping strip as defined in claim 1, wherein said gripping strip element is formed as an injection molded element.

6. A gripping strip as defined in claim 1, wherein said gripping strip element is composed of polyolefin.

7. A gripping strip as defined in claim 6, wherein said gripping strip element is composed of a material selected from the group consisting of polypropylene and polyethylene.

8. A gripping strip as defined in claim 1, wherein said plate-shaped abutment has a grate structure which is open at a side adapted to face the syringe cylinder.

* * * * *